United States Patent [19]
Kaneko et al.

[11] Patent Number: 5,565,489
[45] Date of Patent: Oct. 15, 1996

[54] EPOXYCYCLOHEXENEDIONE DERIVATIVES

[75] Inventors: Masami Kaneko, Sagamihara; Yutaka Saitoh, Machida; Shiro Akinaga, Shizuoka; Masami Okabe, Mishima; Kazuhito Akasaka, Shizuoka; Hirofumi Nakano, Machida, all of Japan

[73] Assignee: Kyowa Hakko Kogyo Co., Ltd., Tokyo, Japan

[21] Appl. No.: 436,359

[22] PCT Filed: Sep. 20, 1994

[86] PCT No.: PCT/JP94/01542

§ 371 Date: May 18, 1995

§ 102(e) Date: May 18, 1995

[87] PCT Pub. No.: WO95/08546

PCT Pub. Date: Mar. 30, 1995

[30] Foreign Application Priority Data

Sep. 22, 1993 [JP] Japan ................................. 5-236178

[51] Int. Cl.$^6$ .................... A61K 31/335; C07D 303/02
[52] U.S. Cl. ............................................. 514/475; 549/546
[58] Field of Search .............................. 549/546; 514/475

[56] References Cited

U.S. PATENT DOCUMENTS 5,106,868  4/1992  Nakano et al. ..................... 514/475

OTHER PUBLICATIONS

Hara et al., PNAS USA, vol. 90 (1993) 2281–85.
Zeeck et al., J. Antibiotics, vol. 40, No. 11 (1987) 1530–40.
Thierickle et al., J. Antibiotics, vol. 40, No. 11 (1987) 1549–54.
Kakinuma et al., J. Am. Chem. Soc., vol. 101, No. 12 (1979) 3402–04.
Gould et al., J. Am. Chem. Soc., vol. 111, No. 20 (1989) 7932–38.
Wipf et al., J. Org. Chem., vol. 59, No. 13 (1994) 3518–19.
Shen et al., Biochemistry, vol. 30, No. 37 (1991) 8936–44.
Schroder et al., Tetrahedron Lett., No. 50 (1973) 4995–98.

*Primary Examiner*—Ba K. Trinh
*Attorney, Agent, or Firm*—Fitzpatrick, Cella, Harper & Scinto

[57] ABSTRACT

The present invention relates to an epoxycyclohexenedione derivative represented by formula (I):

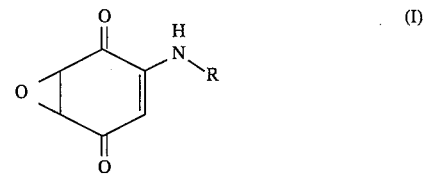

wherein R is a straight-chain or branched alkanoyl group having 10 to 25 carbon atoms, a straight-chain alkenoyl group having 10 to 25 carbon atoms, or a group represented by formula (A):

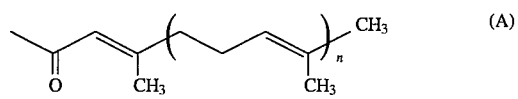

wherein n is an integer of 1 to 4; or a pharmaceutically acceptable salt thereof.

The compounds exhibit antimicrobial activity and antitumor activity.

3 Claims, No Drawings

EPOXYCYCLOHEXENEDIONE DERIVATIVES

This application is a 371 of PCT/JP94/01542 dated Sep. 20, 1994.

TECHNICAL FIELD

The present invention relates to an epoxycyclohexenedione derivative having antimicrobial activity and antitumor activity or a pharmaceutically acceptable salt thereof.

BACKGROUND ART

Ras oncogene undergoes point mutation in many tumor tissues in humans and is detected as an activated form capable of transforming normal cells. It is essential for the expression of transforming activity of the ras oncogene product that the 12th, 13th or 61st amino acid should undergo point mutation and, additionally, the cysteine residue at the C terminal region should be farnesylated for the membrane association of the ras oncogene product. The reaction is catalyzed by farnesyltransferase (hereinafter referred to as "FTase"). Accordingly, an FTase inhibitor is expected to inhibit the function of the ras oncogene product and thereby to have antitumor activity.

Compounds represented by the following formulae are known as expoxycyclohexene derivatives having FTase inhibitory activity.

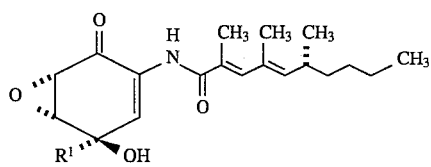

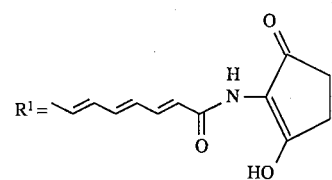

Manumycin [Proc. Natl. Acad. Sci. USA, 90, 2281 (1993)]. It is reported that IC50 against FTase of yeast origin is 5 μmol when ras protein of yeast origin is used as a substrate.

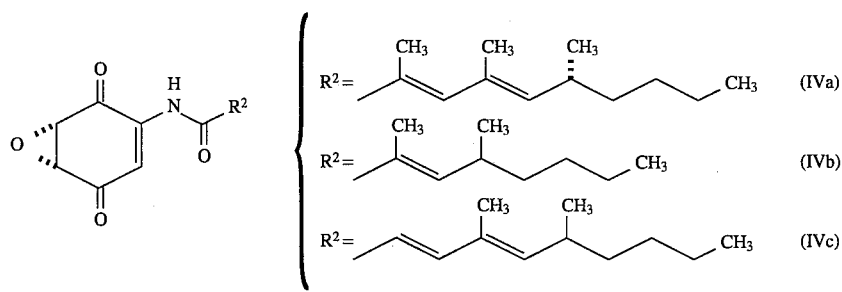

Manumycin derivatives (compounds IVa, IVb, and IVc) [Proc. Natl. Acad. Sci. USA, 90, 2281 (1993); Tetrahedron Letters, (1973); J. Antibiotics, 40, 1530 and 1549 (1987); Japanese Patent Application No. 2-120640, published as unexamined Laid-Open application No. 221377/1992 (U.S. Pat. No. 5,106,868). It is reported that the activity of these compounds can be detected, and that the activity is not numerically described.

An epoxycyclohexenedione derivative represented by the following formula is known, but FTase inhibitory activity of the compound is not reported:

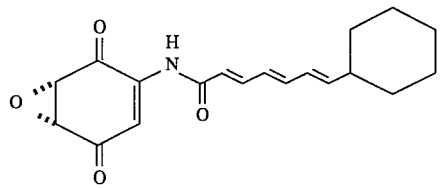

Askamycin derivative [J.Am. Chem. Soc., 101, 3402 (1979)].

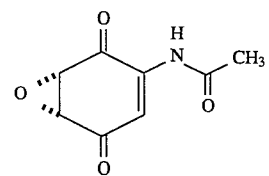

LL-C10037 a derivative [J. Am. Chem. Soc., 111., 7932 (1989), J. Org. Chem., 59, 3518 (1994)].

DISCLOSURE OF THE INVENTION

The present invention relates to an epoxycyclohexenedione derivative represented by formula (I):

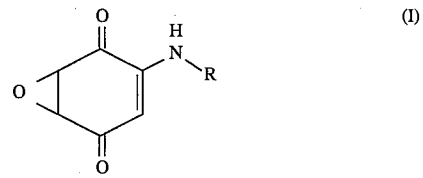

wherein R is a straight-chain or branched alkanoyl group having 10 to 25 carbon atoms, a straight-chain alkenoyl group having 10 to 25 carbon atoms, or a group represented by formula (A):

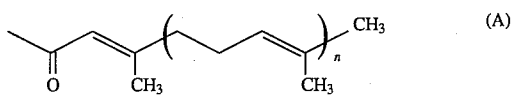

wherein n is an integer of 1 to 4;
or a pharmaceutically acceptable salt thereof.

Hereinafter the compound represented by formula (I) is referred to as Compound I. The same applies to the compounds of other formula numbers.

In the definition of each group in Compound I; the straight-chain or branched alkanoyl group having 10 to 25 carbon atoms includes lauroyl, myristoyl, palmitoyl, stearoyl, 3,7,11-trimethyllauroyl, and 3,7,11,15-tetramethylpalmitoyl; the straight-chain alkenoyl group having 10 to 25 carbon atoms includes palmitoleoyl, linoleoyl, and linolenoyl; and the group represented by formula (A) means geranoyl, farnesoyl, geranylgeranoyl or geranylfarnesoyl.

The pharmaceutically acceptable salts of Compound I include pharmaceutically acceptable acid addition salts, for instance, inorganic acid salts such as hydrochloride, sulfate and phosphate; and organic acid salts such as acetate, maleate, fumarate, tartrate and citrate.

The process for producing Compound I is explained below. Compound I can be prepared by the following steps: acylation of 2-amino-4-methoxyphenol (Step 1), oxidation to quinone (Step 2), and epoxidation (Step 3) as illustrated by the following reaction scheme.

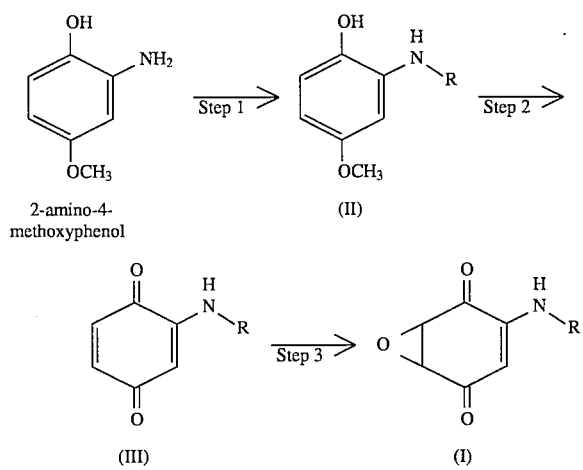

wherein R has the same meaning as defined above.

Step 1:

Compound II can be obtained by reacting 2-amino-4-methoxyphenol with 1 to 2 equivalents of an acyl halide, an acyl anhydride or a mixed acid anhydride having a desired acyl group in the presence of an appropriate base, such as pyridine, N,N-dimethylaniline and N,N-diethylaniline, in a solvent, such as dimethylformamide, dimethylsulfoxide, chloroform, dichloromethane and toluene, or in a solvent such as an appropriate base. The reaction temperature is 0° to 50° C. preferably 20° to 30° C. The reaction period is usually 1 to 48 hours, which is varied with the reaction conditions. The reaction is carried out until the starting material is no longer detectable on thin layer chromatography.

Step 2

Compound III can be obtained by oxidizing Compound II in the presence of 1 to 2 equivalents of an oxidizing agent, such as lead tetraacetate, ammonium cerium (IV) nitrate and [bis(trifluoroacetoxy)iodo]benzene, in a solvent such as tetrahydrofuran, diethyl ether, dioxane, acetonitrile, chloroform, acetic acid, water and a mixture thereof. The reaction temperature is 0° to 50° C., preferably 20° to 30° C. The reaction period is usually 10 to 120 minutes, which is varied with the reaction conditions. The reaction is carried out until the starting material is no longer detectable on thin layer chromatography.

Step 3

Compound I can be obtained by oxidizing Compound III in the presence of 1 to 2 equivalents of a hypochlorite such as sodium hypochlorite and calcium hypochlorite, in a solvent, such as tetrahydrofuran and dioxane. The reaction temperature is preferably −10 to 20° C. The reaction period is usually 10 to 60 minutes, which is varied with the reaction conditions. The reaction is carried out until the starting material is no longer detectable on thin layer chromatography.

The product obtained by the above mentioned processes can be isolated and purified by an appropriate combination of the conventional methods employed in organic synthesis, for instance, filtration, extraction, washing, drying, concentration, crystallization, various kinds of chromatography. The intermediate product may be used for the subsequent reaction without purification.

The compound obtained by the above-mentioned process is usually a mixture of stereoisomers with respect to the configuration of the epoxy group. These isomers can be separated by conventional methods for separation, such as fractional crystallization of a diastereomer, an optically active compound addition salt, or a high performance liquid chromatography (HPLC) using an optically active column.

Compounds I includes stereoisomers, such as geometrical isomers and optical isomers. Mixtures of any possible isomers at any mixing ratio are embraced in the scope of the present invention.

Where a salt of Compound I is desired, a salt of Compound I as produced is purified, or a free compound as obtained is dissolved or suspended in an appropriate solvent, followed by addition of an acid to form a desired salt.

Compounds I or pharmaceutically acceptable salts thereof may exist in the form of an adduct with water or various solvents. These adducts are also included in the present invention.

Examples of Compound I are shown below.

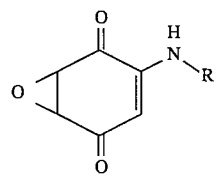

R =

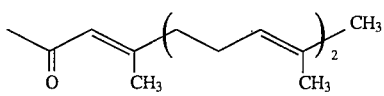

(I-1)

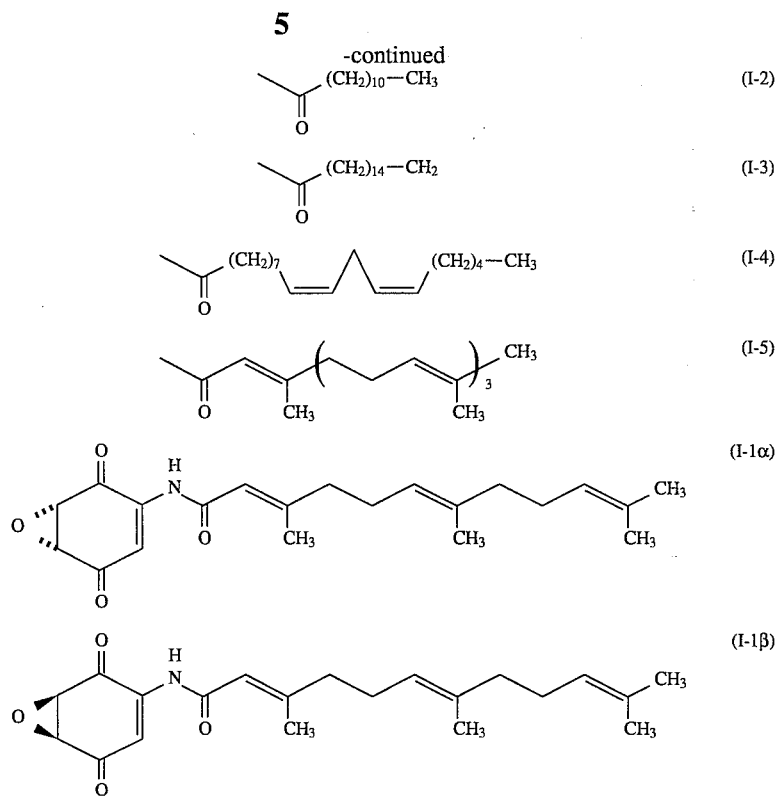

The pharmacological activities of Compound I are explained in the following Test Examples.

Test Example 1

FTase Inhibitory Activity

The FTase used for the assay was obtained from rat brain as follows. An extract of minced brain of a male rat was salted out using ammonium sulfate. The fraction obtained at 50% saturation was dissolved in a buffer solution (20 mM Tris-HCl, pH 7.5, 1 mM dithiothreitol (DTT), 20 μM $ZnCl_2$) and further fractionated by column chromatography using a Mono Q 10/10 column. The column was eluted by gradient elution with 0.3 to 0.4 M NaCl. The active fraction eluted at near 0.35 M NaCl, was used as a partially purified preparation. Measurement of the activity was carried out by using the thus prepared enzyme and v-Ki-ras p21 as a substrate. The v-Ki-ras p21, used as a substrate, was obtained by high expression using *Escherichia coli*, followed by purification according to the method of Tamaoki, et al. [Biochem. Biophys. Res. Commum., 132, 126 (1985)]. [$^3$H]-FPP transferred into v-Ki-ras p21 was determined with a liquid scintillation counter according to the method of Reiss, Y. et al. [Cell, 62, 81 (1990)]. The enzyme inhibitory activity was measured as inhibition of the test compound on farnesylation of the C-terminal of v-ki-ras p21 in the above-mentioned reaction system. The concentration of the test compound inhibiting 50% of the farnesylation ($IC_{50}$) was calculated by comparing the enzyme inhibitory activity of a non-treated group and that of a group treated with the test compound of a known concentration.

The results are shown in Table 1.

TABLE 1

| Compound No. | $IC_{50}$ (μM) |
|---|---|
| Experiment 1 | |
| I-1 | 18 |
| Manumycin | 76 |
| Experiment 2 | |
| IVa | 60 |
| Manumycin | 35 |

According to the result in Table 1 Compound I-1 shows an obvious inhibitory activity against FTase. The inhibitory activity of Compound I-1 is significantly strong as compared with those of manumycin and compound IVa which have been reported as FTase inhibitors.

Test Example 2

FTase Inhibitory Activity

An extract of minced bovine brain was subjected to column chromatography on DEAE-Sephacel (Pharmacia). The active fraction was concentrated by ultrafiltration and dialyzed against a mixture of 20 mM Tris-HCl (pH 8.0), 50 mM NaCl, 20 mM $ZnCl_2$, 1 mM DTT, 0.2 mM phenylmethylsulfonyl fluoride (PMSF). The resulting dialysate was used as a crude enzyme solution. Measurement of activity was carried out by using the enzyme obtained by the above-mentioned method and an FTase [$^3$H]SPA enzyme assay kit (Amersham). Enzyme inhibitory activity was measured as inhibition of farnesylation of the C-terminal peptide of lamin B by the test compound in the above-mentioned reaction system. The enzyme inhibitory activity of a group treated with a test compound of a known concentration was compared with that of a non-treated group to calculate the concentration of the test compound for 50% inhibition of farnesylation ($IC_{50}$).

The results are shown in Table 2.

TABLE 2

| Compound No. | IC$_{50}$ (μM) |
|---|---|
| I-1 | 21 |
| I-2 | 21 |
| I-4 | 19 |
| I-5 | 23 |

According to the results in Table 2, Compounds I-1, 2, 4 and 5 show obvious inhibitory activity against FTase.

Test Example 3

Inhibitory Activity on Cell Growth

The antitumor activity was measured by using NIH 3T3 fibroblasts transformed by oncogene EJ-ras (hereinafter referred to as "NIH 3T3/EJ-ras").

NIH 3T3/EJ-ras cells were suspended in a DME medium (Nissui KK) containing 10% fetal bovine serum, penicillin (100 U/ml) and streptomycin (100 μg/ml) (hereinafter referred to as medium A) in a cell concentration of $1.0 \times 10^4$ cells/ml. Each well of a 24-well microtiter plate was inoculated with 0.1 ml of the cell suspension, and the system was monolayer cultured by incubation in a carbondioxide incubator at 37° C. for 24 hours. To each well was added 0.1 ml of a test compound appropriately diluted with medium A, followed by incubation in the carbondioxide incubator at 37° C. for 72 hours. The cells were recovered by trypsinization, and the number of the cells was counted with a cell counter. A concentration of the test compound for 50% inhibition of cell growth (IC$_{50}$) was calculated.

The result is shown in Table 3.

TABLE 3

| Compound No. | IC$_{50}$ (μM) |
|---|---|
| I-1 | 4.3 |

According to the result in Table 3, Compound I-1 has an obvious inhibitory activity on growth of the NIH 3T3 fibroblasts transformed by oncogene EJ-ras and is useful as an anticancer agent.

Test Example 4

Antimicrobial Activity

Antimicrobial activity was measured by an agar dilution method using a culture medium (pH 7) prepared by dissolving 3 g of Bacto-tryptone (Difco), 3 g of meat extract, 1 g of yeast extract, 1 g of glucose, and 16 g of agar in 1 l of water. The antimicrobial activity was expressed in terms of minimum growth inhibitory concentration (MIC).

The results are shown in Table 4.

TABLE 4

| Compound No. | MIC (μg/ml) | | |
|---|---|---|---|
| | SA | EF | BS |
| I-1 | 0.91 | 0.46 | 0.46 |
| I-2 | >100 | 0.04 | 0.08 |
| I-4 | >100 | 0.33 | 0.65 |
| I-5 | >100 | 0.65 | 0.65 |

SA: *Staphylococcus aureus* ATCC 6538P
EF: *Enterococcus faecium* ATCC 10541
BS: *Bacillus subtilis* No. 10707

According to the results in Table 4, Compounds I-1, 2, 4 and 5 have a remarkable antimicrobial activity and are useful as an antimicrobial agent.

Compound I or a pharmaceutically acceptable salt thereof can be administered orally or parenterally either as such or in various dosage forms, such as tablets, pills, powders, granules, capsules, suppositories, injections and infusions.

The pharmaceutical compositions in the form of the above-mentioned dosage forms can be prepared in a conventional manner. For example, the compositions may contain various vehicles, lubricants, binders, disintegrators, suspending agents, isotonic agents, emulsifiers, and absorption accelerators.

Examples of carriers which can be used in the pharmaceutical compositions are water, injectable distilled water, physiological saline, glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogen phosphate, magnesium stearate, urea, silicone resins, sorbitan fatty acid esters and glycerin fatty acid esters. These carriers are properly selected depending on the dosage form.

The administration schedule of the compound of the present invention is usually 0.01 to 2 mg/kg a day for an injection, infusion, rectal administration using suppositories or application to the skin, depending on the aimed therapeutic effect, the administration route, the period of administration, the age and body weight of a patient, and the like.

Hereinafter, embodiments of the present invention are described by means of Examples and Reference Examples.

EXAMPLE 1

4,5-Epoxy-1-farnesoylamino-3,6-dioxocyclohexene (Compound I-1)

To a solution of 61.0 mg of farnesanic acid in toluene was added 0.04 ml of oxalyl chloride, followed by stirring at room temperature for 3 hours. The solvent was removed by evaporation to give farnesyl chloride as a crude product.

In 2 ml of pyridine was dissolved 31.6 mg of 2-amino-4-methoxyphenol obtained in Reference Example 2, and the farnesyl chloride obtained above was added dropwise to the mixture, followed by stirring at room temperature for 4 hours. The reaction mixture was diluted with ethyl acetate and 2 M hydrochloric acid. The organic layer was washed successively with water and an aqueous saturated solution of sodium hydrogen carbonate, and dryed over sodium sulfate. The solvent was removed by evaporation, and the residue was purified by silica gel chromatography (5/95 ethyl acetate/toluene) to give 46.0 mg (57%) of 2-farnesoylamino-4-methoxyphenol.

Rf 0.38 (ethyl acetate/toluene=1/9)
$^1$HNMR (CDCl$_3$) δ; 1.60 (s, 3H), 1.62 (s, 3H), 1.68 (d, 3H, J=0.76 Hz), 1.99–2.23 (m, 8H), 2.24 (d, 3H, J=0.84 Hz), 3.74 (s, 3H), 5.11 (m, 2H), 5.78 (bs, 1H), 6.59 (d, 1H, J=2.9 Hz), 6.69 (dd, 1H, J=2.9, 8.9 Hz), 6.94 (d, 1H, J=8.9 Hz), 7.33 (bs, 1H).
FAB-MS (M/Z); 356 (M+1)$^+$ In a mixed solvent of 2 ml of tetrahydrofuran and 2 ml of water was dissolved 46.0 mg of 2-farnesoylamino-4-methoxyphenol obtained above, and 69 mg of lead tetraacetate was added to the solution, followed by stirring at room temperature for 30 minutes. The reaction mixture was diluted with ethyl ether and an aqueous saturated solution of sodium hydrogen carbonate. The organic layer was washed with an aqueous saturated solution of sodium chloride and dryed over sodium sulfate. The solvent was removed by evaporation and the residue was purified by silica gel chromatography (ethyl acetate/toluene=5/95) to give 15.7 mg (36%) of 2-farnesoylamino-1,4-benzoquinone.
Rf 0.56 (ethyl acetate/toluene=1/9)
$^1$HNMR (CDCl$_3$) δ; 1.60 (s, 3H), 1.62 (d, 3H, J=1.1 Hz), 1.68 (d, 3H, J=1.1 Hz), 1.98–2.21 (m, 8H), 2.22 (d, 3H, J=1.2 Hz), 5.06–5.11 (m, 2H), 5.75 (d, 1H, J=1.1 Hz), 6.72 (dd, 1H, J=2.3, 10.1 Hz), 6.76 (d, 1H, J=10.1 Hz), 7.64 (d, 1H, J=2.3 Hz), 7.92 (br s, 1H).
FAB-MS (M/Z); 344 (M+3)$^+$ To a solution of 15.0 mg of 2-farnesoylamino-1,4-benzoquinone in 0.05 ml of dioxane was added dropwise 0.045 ml of an aqueous solution of sodium hypochlorite under cooling with water, followed by stirring at room temperature for 30 minutes. A phosphate buffer (pH 7) was added to the reaction mixture, followed by extraction with ethyl acetate. The organic layer was washed with an aqueous saturated solution of sodium chloride and dried over sodium sulfate. The solvent was removed by evaporation, and the residue was purified by silica gel chromatography (ethyl acetate/n-hexane=1/7-dichloromethane/toluene=4/3) to give 1.7 mg (11%) of Compound I-1.
Rf 0.29 (ethyl acetate/n-hexane=2/8)
$^1$HNMR (CDCl$_3$) δ; 1.59 (s, 3H), 1.61 (d, 3H, J=0.9 Hz), 1.67 (d, 3H, J=1.0 Hz), 1.96–2.11 (m, 4H), 2.21 (s, 3H), 2.18–2.24 (m, 4H), 3.81 (dd, 1H, J=2.2, 3.7 Hz), 3.90 (d, 1H, J=3.7 Hz), 5.08 (m, 2H), 5.70 (d, 1H, J=1.0 Hz), 7.59 (d, 1H, J=2.2 Hz), 7.73 (bs, 1H).
FAB-MS (M/Z); 358 (M+1)$^+$ Compound I-1 (racemate) was fractionated by HPLC using a column for optically active compound, CHIRACEL OD (1ø×25 cm), and hexane-isopropyl alcohol (15:1) as an eluent at a flow rate of 4 ml/min. The peaks at retention times of 24 minutes and 26.2 minutes were collected.
Compound I-1β (5S, 6R-form):
HPLC retention time: 24 minutes. The CD spectrum showed a negative Cotton effect at 367 nm and 317 nm.
Compound I-1α (5R, 6S-form):
HPLC retention time: 26.2 minutes. The CD spectrum showed a positive Cotton effect at 366 nm and 317 nm.

The compounds of Examples 2 to 5 described hereinafter were synthesized in a manner similar to that in Example 1 except for using a corresponding acid chloride or anhydride in place of farnesyl chloride.

EXAMPLE 2

4,5-Epoxy-1-lauroylamino-3,6-dioxocyclohexene (Compound I-2)

Rf 0.45 (ethyl acetate/hexane=1/4)
$^1$HNMR (CDCl$_3$) δ; 0.88 (t, 3H, J=6.9 Hz), 1.2–1.4 (m, 16H), 1.67 (quintet, 2H, J=7.5 Hz), 2.40 (t, 2H, J=7.5 Hz), 3.82 (dd, 1H, J=2.2, 3.7 Hz), 3.90 (d, 1H, J=3.7 Hz), 7.54 (d, 1H, J=2.2 Hz), 7.80 (bs, 1H).
FAB-MS (M/Z); 322 (M+1)$^+$

EXAMPLE 3

4,5-Epoxy-1-palmitoylamino-3,6-dioxocyclohexene (Compound I-3)

Rf 0.20 (ethyl acetate/hexane=1/4)
$^1$HNMR (CDCl$_3$) δ; 0.88 (t, 3H, J=7.0 Hz), 1.2–1.4 (m, 24H), 1.67 (quintet, 2H, J=7.5 Hz), 2.40 (t, 2H, J=7.5 Hz), 3.82 (dd, 1H, J=2.3, 3.7 Hz), 3.91 (d, 1H, J=3.7 Hz), 7.54 (d, 1H, J=2.3 Hz), 7.80 (bs, 1H).
FAB-MS (M/Z); 322 (M+1)$^+$

EXAMPLE 4

4,5-Epoxy-1-linoleoylamino-3,6-dioxocyclohexene (Compound I-4)

Rf 0.30 (ethyl acetate/hexane=1/4)
$^1$HNMR (CDCl$_3$) δ; 0.89 (t, 3H, J=6.8 Hz), 1.2–1.4 (m, 14H), 1.67 (quintet, 2H, J=7.0 Hz), 2.05 (q, 4H, J=7.0 Hz), 2.40 (t, 2H, J=7.5 Hz), 2.77 (t, 2H, J=6.8 Hz), 3.82 (dd, 1H, J=2.3, 3.7 Hz), 3.90 (d, 1H, J=3.7 Hz), 5.29–5.41 (m, 4H), 7.54 (d, 1H, J=2.3 Hz), 7.80 (bs, 1H).
FAB-MS (M/Z); 402 (M+1)$^+$

EXAMPLE 5

4,5-Epoxy-1-geranylgeranoylamino-3,6-dioxocyclohexene (Compound I-5)

Rf 0.30 (ethyl acetate/hexane=1/4)
$^1$HNMR (CDCl$_3$) δ; 1.59 (d, 3H, J=0.7 Hz), 1.60 (bs, 3H), 1.62 (bs, 3H), 1.68 (d, 3H, J=1.1 Hz), 1.98 (quintet, 2H, J=7.5 Hz), 2.07 (quintet, 2H, J=7.5 Hz), 2.19–2.21 (m, 7H), 3.81 (dd, 1H, J=2.3, 3.7 Hz), 3.90 (d, 1H, J=3.7 Hz), 5.07–5.11 (m, 3H), 5.70 (bs, 1H), 7.54. (d, 1H, J=2.2 Hz), 7.59 (d, 1H, J=2.3 Hz), 7.73 (bs, 1H).
FAB-MS (M/Z); 426 (M+1)$^+$ Reference Example 1

4-Methoxy-2-nitrophenol

To a stirred solution of 124 mg of 4-methoxyphenol in dichloromethane were added 1 g of silica gel and 0.077 ml of concentrated nitric acid at room temperature. After the completion of the reaction was detected by thin layer chromatography, the reaction mixture was filtered using Cerite. The filtrate was evaporated, and the residue was purified by silica gel chromatography (dichloromethane) to give 98.5 mg (58%) of 4-methoxy-2-nitrophenol.
Rf 0.65 (ethyl acetate/toluene=1/9)
$^1$HNMR (CDCl$_3$) δ; 3.83 (s, 3H), 7.08 (d, 1H, J=9.3 Hz), 7.24 (dd, 1H, J=2.9, 9.3 Hz), 7.51 (d, 1H, J=2.9 Hz), 10.33 (s, 1H).
FAB-MS (M/Z); 168 (M−1)$^-$ Reference Example 2

2-Amino-4-methoxyphenol

In 2.4 ml of ethyl acetate was dissolved 120 mg of 4-methoxy-2-nitrophenol obtained in Reference Example 1, and 12 mg of platinum oxide was added to the mixture, followed by stirring in a hydrogen stream at room temperature for 1 hour. The reaction mixture was filtered using Cerite, and a solution of hydrogen chloride in ethyl acetate was added to the filtrate. The resulting precipitate was collected by filtration and dried to give 111 mg (89%) of 2-amino-4-methoxyphenol.
Rf 0.47 (chloroform/methanol=1/9)
$^1$HNMR (CDCl$_3$) δ; 3.75 (s, 3H), 6.90 (m, 3H).

EFFECT OF THE INVENTION

The present invention provides an epoxycyclohexenedione derivative having antimicrobial activity and antitumor activity or a pharmaceutically acceptable salt thereof.

What is claimed is:

1. An epoxycyclohexenedione derivative represented by formula (I):

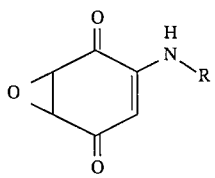

wherein R is a straight-chain or branched alkanoyl group having 10 to 25 carbon atoms, a straight-chain alkenoyl group having 10 to 25 carbon atoms, or a group represented by formula (A):

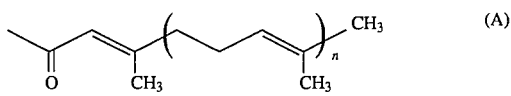

wherein n is an integer of 1 to 4; or a pharmaceutically acceptable salt thereof.

2. A compound according to claim 1 which is selected from the group consisting of 4,5-epoxy-1-farnesoylamino-3,6-dioxocyclohexene, 4,5-epoxy-1-lauroylamino-3,6-dioxocyclohexene, 4,5-epoxy-1-palmitoylamino-3,6-dioxocyclohexene, 4,5-epoxy-1-linoleoylamino-3,6-dioxocyclohexene, 4,5-epoxy-1-geranylgeranoylamino-3,6-dioxocyclohexene, and a pharmaceutically acceptable salt thereof.

3. A pharmaceutical composition comprising a pharmaceutically acceptable carrier and the epoxycyclohexanedione derivative or a pharmaceutically acceptable salt thereof according to claim 1 or 2.

* * * * *

UNITED STATES PATENT AND TRADEMARK OFFICE
CERTIFICATE OF CORRECTION

PATENT NO. : 5,565,489

DATED : October 15, 1996

INVENTOR(S) : MASAMI KANEKO ET AL.

It is certified that error appears in the above-identified patent and that said Letters Patent is hereby corrected as shown below:

COLUMN 1

Line 45, "IC50" should read --$IC_{50}$--.

COLUMN 2

Line 15, "Askamycin" should read --Asukamycin--.

COLUMN 4

Line 23, "above mentioned" should read --above-mentioned--.
Line 37, "Compounds I" should read --Compound I--.
Line 46, "Compounds I" should read --Compound I--.

COLUMN 5

Line 61, "v-ki-ras p21" should read --v-Ki-ras p21--.

UNITED STATES PATENT AND TRADEMARK OFFICE
CERTIFICATE OF CORRECTION

PATENT NO. : 5,565,489

DATED : October 15, 1996

INVENTOR(S) : MASAMI KANEKO ET AL.

It is certified that error appears in the above-identified patent and that said Letters Patent is hereby corrected as shown below:

<u>COLUMN 8</u>

Line 46, "dryed" should read --dried--.
Line 66, "dryed" should read --dried--.

Signed and Sealed this

Eighteenth Day of March, 1997

*Attest:*

BRUCE LEHMAN

*Attesting Officer*      *Commissioner of Patents and Trademarks*